United States Patent [19]

Brun et al.

[11] Patent Number: 6,025,160

[45] Date of Patent: Feb. 15, 2000

[54] POLYNUCLEOTIDE AND POLYPEPTIDE SEQUENCES ENCODING RAT MDR1B2 AND SCREENING METHODS THEREOF

[75] Inventors: Kimberly A Brun, Harleysville, Pa.; Richard J Chenery, Herts, United Kingdom; Harma Ellens, Norristown, Pa.; John A Feild, Wayne, Pa.; Lin Yue, Phoenixville, Pa.

[73] Assignee: SmithKline Beecham Corporation, Philadelphia, Pa.

[21] Appl. No.: 09/120,513

[22] Filed: Jul. 22, 1998

[51] Int. Cl.$^7$ .......................... C12P 21/06; C07H 21/02; C12N 1/20; C12N 15/00; C12N 1/14

[52] U.S. Cl. .................... 435/69.1; 536/23.1; 435/252.3; 435/254.2; 435/348; 435/410; 435/325; 435/320.1

[58] Field of Search ................................ 435/69.1, 320.1, 435/252.3, 254.2; 536/23.1

[56] References Cited

PUBLICATIONS

Watson et al. Recombinant DNA, 2nd edition. Scientific American Books, WH Freeman and Company, pp. 453–470, 1992.

Public Database Accession Nos. M81855, M62425.

Silverman, et al., "Cloning and characterization a member of the rat multidrug resistance (mdr) gene family," *Gene* 106: 229–236, (1991).

*Primary Examiner*—Bradley Sisson
*Assistant Examiner*—Devesh Srivastava
*Attorney, Agent, or Firm*—William T. Han; Ratner & Prestia; William T. King

[57] ABSTRACT

Rat mdr1b2 polypeptides and polynucleotides and method for producing such polypeptides by recombinant techniques are disclosed. Also disclosed are methods for screening for compounds which either agonize or antagonize rat mdr1b2. Further disclosed is method for performing a selection screen, whereby compounds are discovered that neither agonize nor antagonize rat mdr1b2.

11 Claims, No Drawings

POLYNUCLEOTIDE AND POLYPEPTIDE SEQUENCES ENCODING RAT MDR1B2 AND SCREENING METHODS THEREOF

FIELD OF THE INVENTION

This invention relates to newly identified polypeptides and polynucleotides encoding such polypeptides, to their use in identifying compounds which may be agonists, antagonists and/or inhibitors, and to production of such polypeptides and polynucleotides.

BACKGROUND OF THE INVENTION

The drug discovery process is currently undergoing a fundamental revolution as it embraces 'functional genomics', that is, high throughput genome- or gene-based biology. This approach is rapidly superceding earlier approaches based on 'positional cloning'. A phenotype, that is a biological function or genetic disease, would be identified and this would then be tracked back to the responsible gene, based on its genetic map position.

Functional genomics relies heavily on the various tools of bioinformatics to identify gene sequences of potential interest from the many molecular biology databases now available. There is a continuing need to identify and characterise further genes and their related polypeptides/proteins, as targets for drug discovery.

Multi-specific drug transporters are present in cells having a barrier function such as intestinal epithelial and brain microvessel endothelial cells. Other tissues, for example, liver and kidney, also contain multi-specific transporters that can mediate the excretion of drugs and metabolites. Recently, it has been recognized that transporters encoded by genes such as mdr1 contribute to poor intestinal absorption and brain penetration of drugs. Information gained from using multi-specific transporters such as the mdr1 gene product in cell based, membrane based, binding or other assays could enhance drug formulation, selection of formulation excipients, and compound design.

SUMMARY OF THE INVENTION

The present invention relates to rat mdr1b2, in particular rat mdr1b2 polypeptides and rat mdr1b2 polynucleotides, recombinant materials and methods for their production. In another aspect, the invention relates to methods for identifying agonists and antagonists/inhibitors of the rat mdr1b2 gene, as well as compounds than neither agonize nor antagonize the rat mdr1b2 gene. This invention further relates to the generation of in vitro and in vivo comparison data to predict oral absorption and pharmacokinetics in man. Such a comparison of data will enable selection of drugs with optimal pharmacokinetics in man, i.e., good oral bioavailability, brain penetration, plasma half life, and minimum drug interaction.

The present invention further relates to methods for creating transgenic animals and knock-out animals. Furthermore, this invention relates to transgenic and knock-out animals obtained by using these methods. Such animal models are expected to provide valuable insight into the potential pharmacological and toxicological effects in humans of compounds that are discovered by the aforementioned screening methods. An understanding of how the rat mdr1b2 gene functions in these animal models is expected to provide an insight into treating and preventing human diseases including, but not limited to, cancer, inflammation, cardiovascular disease, central nervous system disorders, auto-immune and kidney disease.

DESCRIPTION OF THE INVENTION

In a first aspect, the present invention relates to rat mdr1b2 polypeptides. Such peptides include isolated polypeptides comprising an amino acid sequence which has at least a 99% identity to that of SEQ ID NO: 2 over the entire length of SEQ ID NO: 2. Such polypeptides include those comprising the amino acid of SEQ ID NO: 2.

Further peptides of the present invention include isolated polypeptides in which the amino acid sequence has at least a 99% identity, to the amino acid sequence of SEQ ID NO: 2 over the entire length of SEQ ID NO: 2. Such polypeptides include the polypeptide of SEQ ID NO: 2.

Further peptides of the present invention include isolated polypeptides encoded by a polynucleotide comprising the sequence contained in SEQ ID NO: 1.

Polypeptides of the present invention are believed to be members of the multi-specific drug transporters family of polypeptides. They are therefore of interest because they can be used to establish assays to predict oral absorbtion and pharmacokinetics and thus enhance compound and formulation design. These properties are hereinafter referred to as "rat mdr1b2 activity" or "rat mdr1b2 polypeptide activity" or "biological activity of mdr1b2." Preferably, a polypeptide of the present invention exhibits at least one biological activity of rat mdr1b2.

The polypeptides of the present invention may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

The present invention also includes variants of the aforementioned polypetides, that is polypeptides that vary from the referents by conservative amino acid substitutions, whereby a residue is substituted by another with like characteristics. Typical such substitutions are among Ala, Val, Leu and lie; among Ser and Thr; among the acidic residues Asp and Glu; among Asn and GLn; and among the basic residues Lys and Arg; or aromatic residues Phe and Tyr. Particularly preferred are variants in which several, 5–10, 1–5, 1–3, 1–2 or 1 amino acids are substituted, deleted, or added in any combination.

Polypeptides of the present invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

In a further aspect, the present invention relates to rat mdr1b2 polynucleotides. Such polynucleotides include isolated polynucleotides comprising a nucleotide sequence encoding a polypeptide which has at least a 99% identity to the amino acid sequence of SEQ ID NO: 2, over the entire length of SEQ ID NO: 2. Such polynucleotides include a polynucleotide comprising the nucleotide sequence contained in SEQ ID NO: 1 encoding the polypeptide of SEQ ID NO: 2.

Further polynucleotides of the present invention include isolated polynucleotides comprising a nucleotide sequence that has at least a 99% identity to a nucleotide sequence encoding a polypeptide of SEQ ID NO: 2, over the entire coding region.

Further, polynucleotides of the present invention include isolated polynucleotides comprising a nucleotide sequence which has at least a 99% identity to SEQ ID NO: 1 over the entire length of SEQ ID NO: 1. Such polynucleotides include a polynucleotide comprising the polynucleotide of SEQ ID NO: 1 as well as the polynucleotide of SEQ ID NO: 1.

The invention also provides polynucleotides which are complementary to all the above described polynucleotides. The nucleotide sequence of SEQ ID NO: 1 shows homology with the rat mdr1b gene, which is published by Silverman, J. A., et al., Gene 106: 229–236 (1991). The nucleotide sequence of SEQ ID NO: 1 is a cDNA sequence and comprises a polypeptide encoding sequence (nucleotide 26 to 3853) encoding a polypeptide of 1275 amino acids, the polypeptide of SEQ ID NO: 2. The nucleotide sequence encoding the polypeptide of SEQ ID NO: 2 may be identical to the polypeptide encoding sequence contained in SEQ ID NO: 1 or it may be a sequence other than the one contained in SEQ ID NO: 1, which, as a result of the redundancy (degeneracy) of the genetic code, also encodes the polypeptide of SEQ ID NO: 2. The polypeptide of the SEQ ID NO:2 is structurally related to other proteins of the multi-specific drug transporters family, having homology and/or structural similarity with mdr1b.

Preferred polypeptides and polynucleotides of the present invention are expected to have, inter alia, similar biological functions/properties to their homologous polypeptides and polynucleotides. Furthermore, preferred polypeptides and polynucleotides of the present invention have at least one mdr1b2 activity.

Polynucleotides of the present invention may be obtained, using standard cloning and screening techniques, from a cDNA library derived from mRNA in cells of rat kidney, using the expressed sequence tag (EST) analysis (Adams, M. D., et al. *Science* (1991) 252:1651–1656; Adams, M. D. et al., *Nature* (1992) 355:632–634; Adams, M. D., et al., *Nature* (1995) 377 Supp.: 3–174). Polynucleotides of the invention can also be obtained from natural sources such as genomic DNA libraries or can be synthesized using well known and commercially available techniques.

When polynucleotides of the present invention are used for the recombinant production of polypeptides of the present invention, the polynucleotide may include the coding sequence for the mature polypeptide, by itself; or the coding sequence for the mature polypeptide in reading frame with other coding sequences, such as those encoding a leader or secretory sequence, a pre-, or pro- or prepro- protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz, et al., *Proc Natl Acad Sci USA* (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further embodiments of the present invention include polynucleotides encoding polypeptide variants which comprise the amino acid sequence of SEQ ID NO: 2 and in which several, for instance from 5 to 10, 1 to 5, 1 to 3, 1 to 2 or 1, amino acid residues are substituted, deleted or added, in any combination.

Polynucleotides which are identical or sufficiently identical to a nucleotide sequence contained in SEQ ID NO: 1, may be used as hybridization probes for cDNA and genomic DNA or as primers for a nucleic acid amplification (PCR) reaction, to isolate full-length cDNAs and genomic clones encoding polypeptides of the present invention and to isolate cDNA and genomic clones of other genes (including genes encoding homologs and orthologs from species other than rat) that have a high sequence similarity to SEQ ID NO: 1. Typically these nucleotide sequences are a 99% identical to that of the referent. The probes or primers will generally comprise at least 15 nucleotides, preferably, at least 30 nucleotides and may have at least 50 nucleotides. Particularly preferred probes will have between 30 and 50 nucleotides.

A polynucleotide encoding a polypeptide of the present invention, including homologs and orthologs from species other than rat, may be obtained by a process which comprises the steps of screening an appropriate library under stringent hybridization conditions with a labeled probe having the sequence of SEQ ID NO: 1 or a fragment thereof; and isolating full-length cDNA and genomic clones containing said polynucleotide sequence. Such hybridization techniques are well known to the skilled artisan. Preferred stringent hybridization conditions include overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 microgram/ml denatured, sheared salmon sperm DNA; followed by washing the filters in 0.1×SSC at about 65° C. Thus the present invention also includes polynucleotides obtainable by screening an appropriate library under stringent hybridization conditions with a labeled probe having the sequence of SEQ ID NO: 1 or a fragment thereof.

The skilled artisan will appreciate that, in many cases, an isolated cDNA sequence will be incomplete, in that the region coding for the polypeptide is cut short at the 5' end of the cDNA. This is a consequence of reverse transcriptase, an enzyme with inherently low 'processivity' (a measure of the ability of the enzyme to remain attached to the template during the polymerisation reaction), failing to complete a DNA copy of the mRNA template during 1 st strand cDNA synthesis.

There are several methods available and well known to those skilled in the art to obtain full-length cDNAs, or extend short cDNAs, for example those based on the method of Rapid Amplification of cDNA ends (RACE) (see, for example, Frohman, et al., *Proc. Natl. Acad. Sci., USA* 85, 8998–9002, 1988). Recent modifications of the technique, exemplified by the Marathon™ technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the 'missing' 5' end of the cDNA using a combination of gene specific and adaptor specific oligonucleotide primers. The PCR reaction is then repeated using 'nested' primers, that is, primers designed to anneal within the amplified product (typically an adaptor specific primer that anneals further 3' in the adaptor sequence and a gene specific primer that anneals further 5' in the known gene sequence). The products of this reaction can then be analysed by DNA sequencing and a full-length cDNA constructed either by joining the product directly to the existing cDNA to give a complete sequence, or carrying out a separate full-length PCR using the new sequence information for the design of the 5' primer.

Recombinant polypeptides of the present invention may be prepared by processes well known in the art from genetically engineered host cells comprising expression systems. Accordingly, in a further aspect, the present invention relates to expression systems which comprise a polynucleotide or polynucleotides of the present invention, to host cells which are genetically engineered with such expression systems and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis, etal., BASIC METHODS IN MOLECULAR BIOLOGY (1986) and Sambrook ,et al., MOLECULAR CLONING: A LABORATORY MANUAL, 2nd Ed., Cold Spring Harbor Laboratory Press, Cold Spring Harbor, N.Y. (1989). Preferred such methods include, for instance, calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as *streptococci, staphylococci, E. coli,* Streptoinyces and *Bacillits subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector which is able to maintain, propagate or express a polynucleotide to produce a polypeptide in a host may be used. The appropriate nucleotide sequence may be inserted into an expression system by any of a variety of well-known and routine techniques, such as, for example, those set forth in Sambrook, et al., MOLECULAR CLONING, A LABORATORY MANUAL (supra).

If a polypeptide of the present invention is to be expressed for use in screening assays, it is generally preferred that the polypeptide be produced at the surface of the cell. In this event, the cells may be harvested prior to use in the screening assay.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

The rat mdr1b2 gene products can be expressed in transgenic animals. Animals of any species, including, but not limited to, mice, rats, rabbits, guinea pigs, pigs, micro-pigs, goats, and non-human primates, e.g., baboons, monkeys, chimpanzees, may be used to generate mdr1b2 transgenic animals.

This invention further relates to a method of producing transgenic animals, preferably rats, over-expressing mdr1b2, which method comprises the introduction of several copies of a segment comprising at least the polynucleotide sequence of SEQ ID NO: 1 with a suitable promotor into the cells of a rat embryo at an early stage.

This invention also relates to transgenic animals, characterized in that they are obtained by the method of making transgenic rats, as defined above.

Any technique known in the art may be used to introduce the rat mdr1b2 transgene into animals to produce the founder line of animals. Such techniques include, but are not limited to: pronuclear microinjection (U.S. Pat. No. 4,873, 191); retrovirus mediated gene transfer into germ lines (Van der Putten, et al., *Proc. Natl. Acad. Sci., USA* 82: 6148–6152 (1985); gene targeting in embryonic stem cells (Thompson, et al., *Cell* 56: 313–321 (1989); electrapolation of embryos (Lo, *Mol. Cell Biol.* 3: 1803–1814 (1983); and sperm-mediated gene transfer (Lavitrano, et al., Cell 57: 717–723 (1989); etc. For a review of such techniques, see Gordon, *Intl. Rev. Cytol.* 115: 171–229 (1989).

A further aspect of the present invention involves gene targeting by homologous recombination in embryonic stem cells to produce a transgenic animal with a mutation in the mdr1b2 gene ("knock-out" mutation). In such so-called "knock-out" animals, there is inactivation of the mdr1b2 gene or altered gene expression, such that the animals can be useful to study the function of the mdr1b2 gene, thus providing animals models of human disease, which are otherwise not readily available through spontaneous, chemical or irradiation mutagenesis.

This invention further relates to a method of producing "knock-out" animals, preferably rats, no longer expressing mdr1b2, characterized in that:

a suitable mutation is produced in the polynucleotide sequence of SEQ ID NO: 1 conforming to the invention which inhibits the expression of the gene which encodes the rat mdr1b2;

the said modified SEQ ID NO: 1 is introduced into a segment of rat genomic DNA, combined with an appropriate marker, so as to obtain a labelled sequence containing the modified sequence of SEQ ID NO: 1;

the said modified SEQ ID NO: 1 is integrated in vitro into the stem cells of rat embryo germ lines; then the said stem cells are reinjected into a rat; and after homozygous recombination, homozygous recombinant rats are obtained at the F2 generation which are recognizable by the presence of the marker.

Various methods for producing mutations are contemplated and well known in the art. Preferred is a method where a mutation is generated in a rat mdr1b2 allele the introduction of a DNA construct containing DNA of a gene encoding rat mdr1b2 and the mutation accommodated therein. The mutation is targeted to the allele by way of the DNA construct. The DNA of the gene encoding rat mdr1b2 contained by the construct may be foreign to the species of which the recipient is a member, as in exogenous DNA, or native to the species and foreign only to the individual recipient, as in isogenous DNA, or a mixture of both. The mutation may constitute an insertion, deletion, substitution, or combination thereof. The DNA construct can be introduced by, for example, calcium-phosphate DNA co-precipitation. It is preferred that a mutation be introduced into a electroporation, microinjection, virus infection, ligand-DNA conjugation, virus-ligand-DNA conjugation, and liposomes.

Another embodiment of the instant invention is "knock-out" animals, preferably rats, characterized in that they are obtained by the method of producing recombinant rats as defined above.

The transgenic and "knock-out" animals as defined above are a particularly advantageous model, from a physiological point of view, for studying multi-specific drug transporters. Such animals will be valuable tools to study the function of the rat mdr1b2 gene. Moreover, such animal models are expected to provide information about potential toxicological effects in humans of any compounds that are discovered by the aforementioned screening methods. An understanding of how the rat mdr1b2 gene functions in these animal models is expected to provide an insight into treating and preventing human diseases including, but not limited to, cancer, inflammation, cardiovascular disease, central nervous system disorders, auto-immune and kidney disease.

Polypeptides of the present invention are responsible for many biological functions, including many disease states, in particular the diseases hereinbefore mentioned. It is therefore desirous to devise screening methods to identify compounds which stimulate or which inhibit the function of the polypeptide. Accordingly, in a further aspect, the present invention provides for a method of screening compounds to identify those which stimulate or which inhibit the function of the polypeptide. In general, agonists or antagonists may be employed for therapeutic and prophylactic purposes for such diseases as hereinbefore mentioned. Compounds may be identified from a variety of sources, for example, cells, cell-free preparations, chemical libraries, and natural product mixtures. Such agonists, antagonists or inhibitors so-identified may be natural or modified substrates, ligands, receptors, enzymes, etc., as the case may be, of the polypeptide; or may be structural or functional mimetics thereof (see Coligan, et al., CURRENT PROTOCOLS IN IMMUNOLOGY 1(2): Chapter5 (1991)).

The screening method may simply measure the binding of a candidate compound to the polypeptide, or to cells or membranes bearing the polypeptide, or a fusion protein thereof by means of a label directly or indirectly associated with the candidate compound. Alternatively, the screening method may involve competition with a labeled competitor. Further, these screening methods may test whether the candidate compound results in a signal generated by activation or inhibition of the polypeptide, using detection systems appropriate to the cells bearing the polypeptide. Inhibitors of activation are generally assayed in the presence of a known agonist and the effect on activation by the agonist by the presence of the candidate compound is observed. Constitutively active polypeptides may be employed in screening methods for inverse agonists or inhibitors, in the absence of an agonist or inhibitor, by testing whether the candidate compound results in inhibition of activation of the polypeptide. Further, the screening methods may simply comprise the steps of mixing a candidate compound with a solution containing a polypeptide of the present invention, to form a mixture, measuring rat mdr1b2 activity in the mixture, and comparing the rat mdr1b2 activity of the mixture to a standard. Fusion proteins, such as those made from Fc portion and rat mdr1b2 polypeptide, as hereinbefore described, can also be used for high-throughput screening assays to identify antagonists for the polypeptide of the present invention (see D. Bennett, et al., *J. Mol. Recognition*, 8:52–58 (1995); and K. Johanson, et al., *J. Biol. Chem.*, 270(16):9459–9471 (1995)).

Cell lines can be established which are transfected with the recombinant gene and expressing the transporter gene product. Whole cell or membrane assays can be developed which will evaluate and quantitate the interactions of drugs and test compounds with the transporter.

Examples of potential polypeptide antagonists include antibodies or, in some cases, oligonucleotides or proteins which are closely related to the ligands, substrates, receptors, enzymes, etc., as the case may be, of the polypeptide, e.g., a fragment of the ligands, substrates, receptors, enzymes, etc.; or small molecules which bind to the polypeptide of the present invention but do not elicit a response, so that the activity of the polypeptide is prevented.

Thus, in another aspect, the present invention relates to a screening kit for identifying agonists, antagonists, ligands, receptors, substrates, enzymes, etc. for polypeptides of the present invention; or compounds which decrease or enhance the production of such polypeptides, which comprises:

(a) a polypeptide of the present invention;

(b) a recombinant cell expressing a polypeptide of the present invention;

(c) a cell membrane expressing a polypeptide of the present invention; or (d) antibody to a polypeptide of the present invention;

which polypeptide is preferably that of SEQ ID NO:2.

It will be appreciated that in any such kit, (a), (b), (c) or (d) may comprise a substantial component.

It will be readily appreciated by the skilled artisan that a polypeptide of the present invention may also be used in a method for the structure-based design of an agonist, antagonist or inhibitor of the polypeptide, by:

(a) determining in the first instance the three-dimensional structure of the polypeptide;

(b) deducing the three-dimensional structure for the likely reactive or binding site(s) of an agonist, antagonist or inhibitor;

(c) synthesizing candidate compounds that are predicted to bind to or react with the deduced binding or reactive site; and (d) testing whether the candidate compounds are indeed agonists, antagonists or inhibitors. It will be further appreciated that this will normally be an interactive process.

Multi-specific drug transporters, such as mdr1, are present in cells having a barrier function, such as intestinal epithelial cells, brain microvessel endothelial cells, kidney epithelial cells, and liver hepatocytes. It was recently recognized that these transporters contribute to poor intestinal absorption, poor penetration into the brain, rapid plasma clearance and variability, as well as drug interactions.

In a preferred embodiment, the present invention relates to the use of rat mdr 1 b2 polypeptides, polynucleotides, and recombinant materials thereof in selection screens to identify compounds which are not agonists or antagonist/inhibitors of rat mdr1b2. The data from such a selection screen and a similar screen for human mdri is expected to provide ill vitro and ill vivo comparisons to predict oral absorption, pharmacokinetics in humans. The ability to make such a comparison of data will enhance formulation design through the identification of compounds with optimal development characteristics, i.e., high oral bioavailability, UID (once a day) dosing, reduced drug interactions, reduced variability, and reduced food effects, specifically to avoid interacting with human mdr-1.

The following definitions are provided to facilitate understanding of certain terms used frequently hereinbefore.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Knock-out" refers to partial or complete suppression of the expression of at least a portion of a protein encoded by an endogenous DNA sequence in a cell.

"Transgenic animal" refers to an animal to which foreign DNA has been introduced while the animal is still in its embryonic stage. In most cases, the transgenic approach aims at specific modifications of the genome, e.g., by introducing whole transcriptional units into the genome, or by inactivating pre-existing cellular genes. The targeted character of these procedures sets transgenic technologies apart from experimental methods in which random mutations are conferred to the germline, such as administration of chemical mutagens or treatment with ionizing solution.

"Polynucleotide" generally refers to any polyribonucleotide or polydeoxribonucleotide, which may be unmodified RNA or DNA or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature.

Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (see, for instance, PROTEINS—STRUCTURE AND MOLECULAR PROPERTIES, 2nd Ed., T. E. Creighton, W. H. Freeman and Company, New York, 1993; Wold, F., Post-translational Protein Modifications: Perspectives and Prospects, pgs. 1–12 in POST-TRANSLATIONAL COVALENT MODIFICATION OF PROTEINS, B. C. Johnson, Ed., Academic Press, New York, 1983; Seifter, et al., "Analysis for protein modifications and nonprotein cofactors", *Meth Enzymol* (1990) 182:626–646 and Rattan, et al., "Protein Synthesis: Post-translational Modifications and Aging", *Ann NY Acad Sci* (1992)663:48–62).

"Variant" refers to a polynucleotide or polypeptide that differs from a reference polynucleotide or polypeptide, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity," as known in the art, is a relationship between two or more polypeptide equences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., *SIAM J. Applied Math.*, 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12(1): 387 (1984)), BLASTP, BLASTN, and FASTA (Atschul, S. F., et al., *J. Molec. Biol.* 215: 403–410 (1990). The BLAST X program is publicly available from NCBI and other sources (BLAST Manual, Altschul, S., et al., NCBI NLM NIH Bethesda, MD 20894; Altschul, S., et al., *J. Mol. Biol.* 215: 403–410 (1990). The well known Smith Waterman algorithm may also be used to determine identity.

Preferred parameters for polypeptide sequence comparison include the following:

1) Algorithm: Needleman, et al.,*J. Mol Biol.* 48: 443–453 (1970)

Comparison matrix: BLOSSUM62 from Hentikoff and Hentikoff, *Proc. Natl. Acad. Sci. USA* 89:10915–10919 (1992)

Gap Penalty: 12

Gap Length Penalty: 4

A program useful with these parameters is publicly available as the "gap" program from Genetics Computer Group, Madison Wis. The aforementioned parameters are the default parameters for peptide comparisons (along with no penalty for end gaps).

Preferred parameters for polynucleotide comparison include the following:

1) Algorithm: Needleman, etal.,*J. Mol Biol.* 48: 443–453 (1970)

Comparison matrix: matches =+10, mismatch =0

Gap Penalty: 50

Gap Length Penalty: 3

Available as: The "gap" program from Genetics Computer Group, Madison Wis. These are the default parameters for nucleic acid comparisons.

By way of example, a polynucleotide sequence of the present invention may be identical to the reference sequence of SEQ ID NO: 1, that is be 100% identical, or it may include up to a certain integer number of nucleotide alterations as compared to the reference sequence. Such alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in SEQ ID NO: 1 by the numerical percent of the respective percent identity(divided by 100) and subtracting that product from said total number of nucleotides in SEQ ID NO: 1, or:

$$n_n \leq x_n - (x_n \cdot y),$$

wherein $n_n$ is the number of nucleotide alterations, $x_n$ is the total number of nucleotides in SEQ ID NO: 1, and y is, for instance, 0.70 for 70%, 0.80 for 80%, 0.85 for 85%, 0.90 for 90%, for 95%, etc., and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

Similarly, a polypeptide sequence of the present invention may be identical to the reference sequence of SEQ ID NO: 2, that is be 100% identical, or it may include up to a certain integer number of amino acid alterations as compared to the reference sequence such that the % identity is less than 100%. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO: 2 by the numerical percent of the respective percent identity (divided by 100) and then subtracting that product from said total number of amino acids in SEQ ID NO: 2, or:

$$n_a \leq x_a - (x_a \cdot y),$$

wherein $n_a$ is the number of amino acid alterations, $x_a$ is the total number of amino acids in SEQ ID NO: 2, and y is, for instance 0.70 for 70%, 0.80 for 80%, 0.85 for 85% etc., and wherein any non-integer product of $x_a$ and y is rounded down to the nearest integer prior to subtracting it from $x_a$.

"Fusion protein" refers to a protein encoded by two, often unrelated, fused genes or fragments thereof. In one example, EP-A-0 464 discloses fusion proteins comprising various portions of constant region of immunoglobulin molecules together with another human protein or part thereof. In many cases, employing an immunoglobulin Fc region as a part of a fusion protein is advantageous for use in therapy and diagnosis resulting in, for example, improved pharmacokinetic properties [see, e.g., EP-A 0232 262]. On the other hand, for some uses it would be desirable to be able to delete the Fe part after the fusion protein has been expressed, detected and purified.

All publications, including but not limited to patents and patent applications, cited in this specification are herein incorporated by reference as if each individual publication were specifically and individually indicated to be incorporated by reference herein as though fully set forth.

| SEQUENCE INFORMATION |
| --- |
| SEQ ID NO:1 |

GAATTCGGCTTTACGTGAGGCCACCATG-
GAGTTTGAAGAGGGCCTTAACGGAACAGCAGA

CAAGAACTTCTCAAAGATGGGCAAAAA-
GAGTAAAAAGGAGAAGGAGAAGAAACCTGCTGT

TGGCATATTCGGGATGTTTCGCTATGCA-
GATTGGCTTGACAAGCTGTGCATGGCTCTGGG

AACTCTCGCTGCTATCATCCACGGAAC-
CCTGCTTCCCCTCCTGATGCTGGTGTTCGGATA

CATGACAGATAGTTTTACCCAAGCA-
GAGACCCGCATTCTGCCGAGCGTTACTAATCAAAG

TGAAATCAACAGTACACAGACCGTCAGC-
GACAGCAGTCTGGAGGAGGACATGGCCATGTA

CGCCTACTATTACACGGGCATTGGTGC-
CGGTGTGCTCATCGTTGCCTACATCCAGGTTTC

ACTTTGGTGCCTGGCAGCTGGGAGA-
CAAATACACAAGATTAGGCAGAAGTTTTTCCATGC

CATCATGAATCAGGAGATAGGCTG-
GTTTGACGTGAATGACGCTGGGGAGCTCAACACCCG

GCTCACAGATGACGTCTCCAAAATTAAT-
GACGGAATTGGTGACAAACTTGGAATGTTCTT

TCAGTCCATAACGACATTTTCAGCCG-
GTTTTATAATAGGATTTATAAGTGGTTGGAAGCT

AACCCTTGTAATTTTGGCCGTCAGC-
CCTCTTATTGGGTTGTCATCTGCCATGTGGGCAAA

GGTACTGACTTCATTTACTAATAAG-
GAACTCCAGGCTTATGCGAAAGCTGGAGCAGTTGC

CGAAGAAGTCTTAGCAGCCATCAGAACT-
GTGATTGCGTTTGGAGGACAAAAGAAGGAACT

TGAAAGGTACAATAAAAATTTAGAA-
GAAGCTAAAAGAGTTGGCATAAAGAAAGCCATCAC

GGCCAACATTTCCATAGGTATTGCCTAC-
CTGTTGGTCTATGCGTCTTATGCACTGGCATT

CTGGTATGGGACCTCCTTGGTCCTCT-
CAAATGAATATTCTATTGGACAAGTGCTTACCGT

CTTCTTCTCTATTTTATTGGG-
GACTTTCAGTATTGGACATTTAGCCCCAAACATAGAAGC

CTTTGCAAATGCAAGAGGGGCAGCCTAT-
GAAATCTTCAAGATAATTGATAATGAGCCAAG

CATTGACAGCTTCTCAACCAAGGGACA-
CAAACCAGACAGTATAATGGGAAATTTGGAATT

TAAAAATGTTTACTTCAACTACCCAT-
CACGAAGTGAAGTTAAGATCTTGAAGGGCCTCAA

CCTGAAGGTGAAGAGCGGGCAGACGG-
TAGCCCTGGTTGGCAACAGTGGCTGTGGGAAAAG

CACAACTGTCCAGCTGCTGCAGAGGCTC-
TACGACCCCATAGAGGGCGAGGTCAGTATCGA

CGGACAGGACATCAGGACCATCAATGT-
GAGGTATCTGCGGGAAATCATTGGGGTGGTGAG

TCAGGAACCCGTGCTGTTTGCCACCAC-
GATTGCCGAAAACATTCGCTATGGCCGAGAAAA

CGTCACCATGGATGAGATAGAGAAAGCT-
GTCAAGGAAGCCAATGCCTATGACTTCATCAT

-continued

SEQUENCE INFORMATION

GAAACTGCCCCACAAATTTAACACCCTG-
GTTGGTGAGAGAGGGGCGCAGCTGAGTGGGGG

ACAGAAACAGAGGATCGCCATTGC-
CCGGGCCCTGGTCCGCAACCCCAAGATCCTTTTGTT

GGATGAGGCCACGTCAGCCTTGGACACA-
GAAAGCGAAGCCGTGGTTCAGGCCGCTCTGGA

TAAGGCTAGAGAAGGCCGGACCACCAT-
TGTGATAGCTCACCGCTTGTCTACAGTGCGCAA

TGCTGACGTCATTGCTGGTTTTGATG-
GTGGTGTCATTGTGGAGCAAGGAAATCATGAAGA

GCTCATGAAAGAGAAGGGCATTTACT-
TCAAACTTGTCATGACACAGACTAGAGGAAATGA

AATTGAACCAGGAAATAATGCTTAT-
GAATCCCAAAGTGACACTGGTGCCTCTGAGTTGAC

TTCAGAAAAATCAAAATCTCCTT-
TAATAAGGAGATCAATTCGCAGAAGTATCCACAGAAG

ACAAGACCAGGAGAGAAGACTTAGTTC-
GAAAGAGGATGTGGATGAAGATGTGCCTATGGT

TTCCTTTTGGCAGATC-
CTAAAGCTAAATATTAGTGAATGGCCCTATTTAGTTGTGGGTGT

ACTTTGTGCTGTTATAAATGGGTGCATA-
CAACCAGTGTTTGCCATAGTGTTTTCAAAGAT

TGTAGGGGTTTTTTCAAGAGACGACGAC-
CATGAAACCAAACAACGGAATTGTAACTTGTT

TTCCCTTCTCTTTCTGGTCATGGGAAT-
GATTTCTTTTGTTACGTACTTCTTTCAAGGCTT

CACATTTGGCAAAGCTGGAGAGATCCT-
CACCAAGCGACTCCGATACATGGTCTTCAAATC

CATGCTGCGACAGGATATAAGCTG-
GTTTGATGACCATAAAAACACCACTGGCTCGCTGAC

TACCAGGCTCGCTAGTGACGCTTCTAAT-
GTTAAAGGGGCTATGGGCTCCAGGCTTGCTGT

AGTTACCCAGAATGTAGCAAACCTTG-
GCACAGGAATTATCTTATCCTTAGTCTATGGCTG

GCAGCTTACACTTTTACTTGTAGTAAT-
TATACCACTCATTGTCTTGGGTGGAATTATTGA

AATGAAACTGTTGTCTGGTCAAGCCT-
TGAAGGACAAGAAAGAGCTAGAGATCTCTGGGAA

GATCGCTACAGAAGCAATTGAAAACTTC-
CGCACTGTTGTCTCTTTGACTAGGGAGCAGAA

GTTTGAAACTATGTATGCCCAGAGCTTG-
CAGATACCATACAGAAATGCTTTGAAGAAAGC

ACACGTCTTTGGGATCACCTTCGCCT-
TCACCCAGGCCATGATTTATTTTTCCTATGCTGC

TTGTTTCCGGTTCGGTGCCTACTTGGTG-
GCACGAGAACTCATGACGTTTGAAAATGTTAT

GTTGGTATTTTCTGCTGTTGTCTTTGGT-
GCCATGGCAGCAGGGAATACCAGTTCATTCGC

TCCTGACTACGCGAAGGCCAAAGTCT-
CAGCATCCCACATCATCAGGATCATTGAGAAAAT

CCCCGAGATTGACAGCTACAGCACG-
GAGGGCTTGAAGCCTAATTGGTTAGAAGGAAATGT

GAAATTTAATGGAGTCATGTTCAAC-
TATCCCACCCGACCCAACATCCCAGTGCTTCAGGG

-continued

SEQUENCE INFORMATION

ACTGAGCTTCGAGGTGAA-
GAAGGGGCAAACGCTTCGCCTGGTGGGCAGCAGTGGCTGCGG

GAAGAGTACAGTGGTCCAGCTGCTC-
GAGCGCTTCTACAACCCCATGGCTGGAACAGTGTT

TCTAGATGGCAAAGAAATAAAACAACT-
CAACGTCCAGTGGCTCCGCGCCCACCTGGGCAT

TGTGTCCCAGGAGCCCATCCT-
GTTTGACTGCAGCATCACCGAGAACATCGCCTACGGAGA

CAACAGCCGTGTCGTGTCTCATGAG-
GAGATCGTGAGGGCCGCCAGGGAGGCCAACATCCA

CCAGTTCATCGACTCACTGCCT-
GAGAAATACAACACCAGAGTGGGAGACAAAGGGACTCA

GCTGTCGGGCGGGCAGAAGCAGCG-
CATCGCCATCGCGCGCGCCCTCGTCAGACAGCCTCA

CATCTTACTTCTGGATGAAGCGACAT-
CAGCTCTGGATACGGAGAGTGAAAAGGTCGTCCA

GGAAGCGCTGGACAAAGCCAGGGAAGGC-
CGCACCTGCATTGTGATCGCGCACCGCCTGTC

CACCATCCAGAACGCAGACTTGATCGTG-
GTGATTCAGAACGGCCAGGTCAAGGAGCACGG

CACCCACCAGCAGCTGCTGGCCCA-
GAAAGGCATCTATTTCTCGATGGTTCAGGCTGGAGC

AAAGCGCTCATGAGCTGGGAG-
TATTTGAGGTGCTAAGTATTTCTAATATTGGTGTTCAAA

CATGGCACGTAACCAAAGTTAAAAGGT-
TAAAAGCACTGTTAAAGGTAATTTCATCAAGAC

GAGAAGCCTTCAGAGACTTCATAAT-
TAAATGAACCGAAATTGAAAAAAAAATCATTAAAC

AGGGCCACATTTTTTAATTGTATTATGT-
GATTCAAGAGAACATATAGTTTTTTTTAAAAA

GAAATGTGTAGTTTTGTTTCAGTTTTTT-
TAATTTCTACCCTATTCCCTTAAATGATCATA

AAGGCTGTAAAAAGCACTATTTTTT-
TAAATTGCCTATAAAAATTAAATTTTCATAAAAAA

AAAAAAAAAAAACTCGAGGGGGGGCCCGGTACC

SEQ ID NO:2

MEFEEGLNGTADKNFSK-
MGKKSKKEKEKKPAVGIFGMFRYADWLDKLCMALGTLAAIIHG

TLLPLLMLVFGYMTDSFTQAETRILPS-
VTNQSEINSTQTVSDSSLEEDMAMYAYYYTGIG

AGVLIVAYIQVSLWCLAAGRQIHKIRQK-
FFHAIMNQEIGWFDVNDAGELNTRLTDDVSKI

NDGIGDKLGMFFQSITTFSAGFIIGFIS-
GWKLTLVILAVSPLIGLSSAMWAKVLTSFTNK

ELQAYAKAGAVAEEVLAAIRTVIAFG-
GQKKELERYNKNLEEAKRVGIKKAITANISIGIA

YLLVYASYALAFWYGTSLVLSNEY-
SIGQVLTVFFSILLGTFSIGHLAPNIEAFANARGAA

YEIFKIIDNEPSIDSFSTKGHKPD-
SIMGNLEFKNVYFNYPSRSEVKILKGLNLKVKSGQT

VALVGNSGCGKSTTVQLLQRLYDPIE-
GEVSIDGQDIRTINVRYLREIIGVVSQEPVLFAT

TIAENIRYGRENVTMDEIEKAVKEANAY-
DFIMKLPHKFNTLVGERGAQLSGGQKQRIAIA

-continued

SEQUENCE INFORMATION

RALVRNPKILLLDEATSALDTESEAV-
VQAALDKAREGRTTIVIAHRLSTVRNADVIAGFD

GGVIVEQGNHEELMKEKGIY-
FKLVMTQTRGNEIEPGNNAYESQSDTGASELTSEKSKSPL

IRRSIRRSIHRRQDQERRLSSKEDVDED-
VPMVSFWQILKLNISEWPYLVVGVLCAVINGC

IQPVFAIVFSKIVGVFSRDDDHET-
KQRNCNLFSLLFLVMGMISFVTYFFQGFTFGKAGEI

LTKRLRYMVFKSMLRQDISWFDDHKNT-
TGSLTTRLASDASNVKGAMGSRLAVVTQNVANL

GTGIILSLVYGWQLTLLLVVIIPLIVLGGIIEMKLLSGQALKEKKELEISGKIATEAIEN

FRTVVSLTREQKFETMYAQSLQIPYR-
NALKKAHVFGITFAFTQAMIYFSYAACFRFGAYL

VARELMTFENVMLVFSAVVFGAM-
AAGNTSSFAPDYAKAKVSASHIIRIIEKIPEIDSYST

EGLKPNWLEGNVKFNGVMFNYPTRP-
NIPVLQGLSFEVKKGQTLRLVGSSGCGKSTVVQLL

ERFYNPMAGTVFLDGKEIKQLNVQWL-
RAHLGIVSQEPILFDCSITENIAYGDNSRVVSHE

EIVRAAREANIHQFIDSLPEKYNTRVGD-
KGTQLSGGQKQRIAIARALVRQPHILLLDEAT

SALDTESEKVVQEALDKAREGRTCIVI-
AHRLSTIQNADLIVVIQNGQVKEHGTHQQLLAQ

KGIYFSMVQAGAKRS

What is claimed is:

1. An isolated polynucleotide comprising a nucleotide sequence encoding a polypeptide comprising the amino acid sequence set forth in SEQ ID NO:2.

2. An expression vector comprising a polynucleotide capable of producing a polypeptide comprising the amino acid sequence of SEQ ID NO:2 when said expression vector is present in a compatible host cell.

3. A process for producing a recombinant host cell comprising transforming or transfecting a host cell with the expression vector of claim 2 such that the host cell, under appropriate culture conditions, produces a polypeptide comprising the amino acid sequence set forth in SEQ ID NO:2.

4. A recombinant host cell produced by the process of claim 3.

5. A membrane containing the recombinant host cell of claim 4 expressing a polypeptide comprising the amino acid sequence set forth in SEQ ID NO:2.

6. A process for producing a polypeptide comprising the amino acid sequence set forth in SEQ ID NO:2, said process comprising culturing the recombinant host cell of claim 5 under conditions sufficient for the production of said polypeptide and recovering said polypeptide from the culture.

7. The isolated polynucleotide of claim 1 comprising the polynucleotide set forth in SEQ ID NO: 1.

8. The isolated polynucleotide of claim 1 comprising nucleotides 26 to 3853 of the polynucleotide set forth in SEQ ID NO: 1.

9. An isolated polynucleotide which is fully complementary to a nucleotide sequence encoding the amino acid sequence set forth in SEQ ID NO:2.

10. The isolated polynucleotide of claim 9 which is fully complementary to the polynucleotide set forth in SEQ ID NO: 1.

11. The isolated polynucleotide of claim 9 which is fully complementary to nucleotides 26 to 3853 of the polynucleotide set forth in SEQ ID NO:1.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 4233 base pairs
       (B) TYPE: nucleic acid
       (C) STRANDEDNESS: single
       (D) TOPOLOGY: linear (ii) MOLECULE TYPE: Genomic DNA (xi) SEQUENCE DESCRIPTION: SEQ ID NO:1:

```
GAATTCGGCT TTACGTGAGG CCACCATGGA GTTTGAAGAG GGCCTTAACG GAACAGCAGA      60

CAAGAACTTC TCAAAGATGG GCAAAAAGAG TAAAAAGGAG AAGGAGAAGA AACCTGCTGT     120

TGGCATATTC GGGATGTTTC GCTATGCAGA TTGGCTTGAC AAGCTGTGCA TGGCTCTGGG     180

AACTCTCGCT GCTATCATCC ACGGAACCCT GCTTCCCCTC CTGATGCTGG TGTTCGGATA     240

CATGACAGAT AGTTTTACCC AAGCAGAGAC CCGCATTCTG CCGAGCGTTA CTAATCAAAG     300

TGAAATCAAC AGTACACAGA CCGTCAGCGA CAGCAGTCTG GAGGAGGACA TGGCCATGTA     360

CGCCTACTAT TACACGGGCA TTGGTGCCGG TGTGCTCATC GTTGCCTACA TCCAGGTTTC     420

ACTTTGGTGC CTGGCAGCTG GGAGACAAAT ACACAAGATT AGGCAGAAGT TTTTCCATGC     480
```

```
CATCATGAAT CAGGAGATAG GCTGGTTTGA CGTGAATGAC GCTGGGGAGC TCAACACCCG    540

GCTCACAGAT GACGTCTCCA AAATTAATGA CGGAATTGGT GACAAACTTG GAATGTTCTT    600

TCAGTCCATA ACGACATTTT CAGCCGGTTT TATAATAGGA TTTATAAGTG GTTGGAAGCT    660

AACCCTTGTA ATTTTGGCCG TCAGCCCTCT TATTGGGTTG TCATCTGCCA TGTGGGCAAA    720

GGTACTGACT TCATTTACTA ATAAGGAACT CCAGGCTTAT GCGAAAGCTG GAGCAGTTGC    780

CGAAGAAGTC TTAGCAGCCA TCAGAACTGT GATTGCGTTT GGAGGACAAA AGAAGGAACT    840

TGAAAGGTAC AATAAAAATT TAGAAGAAGC TAAAAGAGTT GGCATAAAGA AAGCCATCAC    900

GGCCAACATT TCCATAGGTA TTGCCTACCT GTTGGTCTAT GCGTCTTATG CACTGGCATT    960

CTGGTATGGG ACCTCCTTGG TCCTCTCAAA TGAATATTCT ATTGGACAAG TGCTTACCGT   1020

CTTCTTCTCT ATTTTATTGG GGACTTTCAG TATTGGACAT TTAGCCCCAA ACATAGAAGC   1080

CTTTGCAAAT GCAAGAGGGG CAGCCTATGA AATCTTCAAG ATAATTGATA ATGAGCCAAG   1140

CATTGACAGC TTCTCAACCA AGGGACACAA ACCAGACAGT ATAATGGGAA ATTTGGAATT   1200

TAAAAATGTT TACTTCAACT ACCCATCACG AAGTGAAGTT AAGATCTTGA AGGGCCTCAA   1260

CCTGAAGGTG AAGAGCGGGC AGACGGTAGC CCTGGTTGGC AACAGTGGCT GTGGGAAAAG   1320

CACAACTGTC CAGCTGCTGC AGAGGCTCTA CGACCCCATA GAGGGCGAGG TCAGTATCGA   1380

CGGACAGGAC ATCAGGACCA TCAATGTGAG GTATCTGCGG GAAATCATTG GGGTGGTGAG   1440

TCAGGAACCC GTGCTGTTTG CCACCACGAT TGCCGAAAAC ATTCGCTATG GCCGAGAAAA   1500

CGTCACCATG GATGAGATAG AGAAAGCTGT CAAGGAAGCC AATGCCTATG ACTTCATCAT   1560

GAAACTGCCC CACAAATTTA ACACCCTGGT TGGTGAGAGA GGGGCGCAGC TGAGTGGGGG   1620

ACAGAAACAG AGGATCGCCA TTGCCCGGGC CCTGGTCCGC AACCCCAAGA TCCTTTTGTT   1680

GGATGAGGCC ACGTCAGCCT TGGACACAGA AAGCGAAGCC GTGGTTCAGG CCGCTCTGGA   1740

TAAGGCTAGA GAAGGCCGGA CCACCATTGT GATAGCTCAC CGCTTGTCTA CAGTGCGCAA   1800

TGCTGACGTC ATTGCTGGTT TTGATGGTGG TGTCATTGTG GAGCAAGGAA ATCATGAAGA   1860

GCTCATGAAA GAGAAGGGCA TTTACTTCAA ACTTGTCATG ACACAGACTA GAGGAAATGA   1920

AATTGAACCA GGAAATAATG CTTATGAATC CCAAAGTGAC ACTGGTGCCT CTGAGTTGAC   1980

TTCAGAAAAA TCAAAATCTC CTTTAATAAG GAGATCAATT CGCAGAAGTA TCCACAGAAG   2040

ACAAGACCAG GAGAGAAGAC TTAGTTCGAA AGAGGATGTG GATGAAGATG TGCCTATGGT   2100

TTCCTTTTGG CAGATCCTAA AGCTAAATAT TAGTGAATGG CCCTATTTAG TTGTGGGTGT   2160

ACTTTGTGCT GTTATAAATG GGTGCATACA ACCAGTGTTT GCCATAGTGT TTTCAAAGAT   2220

TGTAGGGGTT TTTTCAAGAG ACGACGACCA TGAAACCAAA CAACGGAATT GTAACTTGTT   2280

TTCCCTTCTC TTTCTGGTCA TGGGAATGAT TTCTTTTGTT ACGTACTTCT TTCAAGGCTT   2340

CACATTTGGC AAAGCTGGAG AGATCCTCAC CAAGCGACTC CGATACATGG TCTTCAAATC   2400

CATGCTGCGA CAGGATATAA GCTGGTTTGA TGACCATAAA AACACCACTG GCTCGCTGAC   2460

TACCAGGCTC GCTAGTGACG CTTCTAATGT TAAAGGGGCT ATGGGCTCCA GGCTTGCTGT   2520

AGTTACCCAG AATGTAGCAA ACCTTGGCAC AGGAATTATC TTATCCTTAG TCTATGGCTG   2580

GCAGCTTACA CTTTTACTTG TAGTAATTAT ACCACTCATT GTCTTGGGTG GAATTATTGA   2640

AATGAAACTG TTGTCTGGTC AAGCCTTGAA GGACAAGAAA GAGCTAGAGA TCTCTGGGAA   2700

GATCGCTACA GAAGCAATTG AAAACTTCCG CACTGTTGTC TCTTTGACTA GGGAGCAGAA   2760

GTTTGAAACT ATGTATGCCC AGAGCTTGCA GATACCATAC AGAAATGCTT TGAAGAAAGC   2820

ACACGTCTTT GGGATCACCT TCGCCTTCAC CCAGGCCATG ATTTATTTTT CCTATGCTGC   2880
```

```
TTGTTTCCGG TTCGGTGCCT ACTTGGTGGC ACGAGAACTC ATGACGTTTG AAAATGTTAT    2940

GTTGGTATTT TCTGCTGTTG TCTTTGGTGC CATGGCAGCA GGGAATACCA GTTCATTCGC    3000

TCCTGACTAC GCGAAGGCCA AAGTCTCAGC ATCCCACATC ATCAGGATCA TTGAGAAAAT    3060

CCCCGAGATT GACAGCTACA GCACGGAGGG CTTGAAGCCT AATTGGTTAG AAGGAAATGT    3120

GAAATTTAAT GGAGTCATGT TCAACTATCC CACCCGACCC AACATCCCAG TGCTTCAGGG    3180

ACTGAGCTTC GAGGTGAAGA AGGGGCAAAC GCTTCGCCTG GTGGGCAGCA GTGGCTGCGG    3240

GAAGAGTACA GTGGTCCAGC TGCTCGAGCG CTTCTACAAC CCCATGGCTG AACAGTGTT    3300

TCTAGATGGC AAAGAAATAA ACAACTCAA CGTCCAGTGG CTCCGCGCCC ACCTGGGCAT    3360

TGTGTCCCAG GAGCCCATCC TGTTTGACTG CAGCATCACC GAGAACATCG CCTACGGAGA    3420

CAACAGCCGT GTCGTGTCTC ATGAGGAGAT CGTGAGGGCC GCCAGGGAGG CCAACATCCA    3480

CCAGTTCATC GACTCACTGC CTGAGAAATA CAACACCAGA GTGGGAGACA AGGGACTCA    3540

GCTGTCGGGC GGGCAGAAGC AGCGCATCGC CATCGCGCGC GCCCTCGTCA GACAGCCTCA    3600

CATCTTACTT CTGGATGAAG CGACATCAGC TCTGGATACG GAGAGTGAAA AGGTCGTCCA    3660

GGAAGCGCTG GACAAAGCCA GGGAAGGCCG CACCTGCATT GTGATCGCGC ACCGCCTGTC    3720

CACCATCCAG AACGCAGACT TGATCGTGGT GATTCAGAAC GGCCAGGTCA AGGAGCACGG    3780

CACCCACCAG CAGCTGCTGG CCCAGAAAGG CATCTATTTC TCGATGGTTC AGGCTGGAGC    3840

AAAGCGCTCA TGAGCTGGGA GTATTTGAGG TGCTAAGTAT TTCTAATATT GGTGTTCAAA    3900

CATGGCACGT AACCAAAGTT AAAAGGTTAA AAGCACTGTT AAAGGTAATT TCATCAAGAC    3960

GAGAAGCCTT CAGAGACTTC ATAATTAAAT GAACCGAAAT TGAAAAAAAA ATCATTAAAC    4020

AGGGCCACAT TTTTTAATTG TATTATGTGA TTCAAGAGAA CATATAGTTT TTTTTAAAAA    4080

GAAATGTGTA GTTTTGTTTC AGTTTTTTTA ATTTCTACCC TATTCCCTTA AATGATCATA    4140

AAGGCTGTAA AAAGCACTAT TTTTTTAAAT TGCCTATAAA AATTAAATTT TCATAAAAAA    4200

AAAAAAAAAA AACTCGAGGG GGGGCCCGGT ACC                                4233

(2) INFORMATION FOR SEQ ID NO:2:

(i) SEQUENCE CHARACTERISTICS:
        (A) LENGTH: 1275 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Met Glu Phe Glu Glu Gly Leu Asn Gly Thr Ala Asp Lys Asn Phe Ser
 1               5                  10                  15

Lys Met Gly Lys Lys Ser Lys Lys Glu Lys Glu Lys Lys Pro Ala Val
                20                  25                  30

Gly Ile Phe Gly Met Phe Arg Tyr Ala Asp Trp Leu Asp Lys Leu Cys
            35                  40                  45

Met Ala Leu Gly Thr Leu Ala Ala Ile Ile His Gly Thr Leu Leu Pro
        50                  55                  60

Leu Leu Met Leu Val Phe Gly Tyr Met Thr Asp Ser Phe Thr Gln Ala
65                  70                  75                  80

Glu Thr Arg Ile Leu Pro Ser Val Thr Asn Gln Ser Glu Ile Asn Ser
                85                  90                  95

Thr Gln Thr Val Ser Asp Ser Ser Leu Glu Glu Asp Met Ala Met Tyr
```

-continued

```
                100                 105                 110
Ala Tyr Tyr Tyr Thr Gly Ile Gly Ala Gly Val Leu Ile Val Ala Tyr
            115                 120                 125
Ile Gln Val Ser Leu Trp Cys Leu Ala Ala Gly Arg Gln Ile His Lys
    130                 135                 140
Ile Arg Gln Lys Phe Phe His Ala Ile Met Asn Gln Glu Ile Gly Trp
145                 150                 155                 160
Phe Asp Val Asn Asp Ala Gly Glu Leu Asn Thr Arg Leu Thr Asp Asp
                165                 170                 175
Val Ser Lys Ile Asn Asp Gly Ile Asp Lys Leu Gly Met Phe Phe
            180                 185                 190
Gln Ser Ile Thr Thr Phe Ser Ala Gly Phe Ile Ile Gly Phe Ile Ser
    195                 200                 205
Gly Trp Lys Leu Thr Leu Val Ile Leu Ala Val Ser Pro Leu Ile Gly
210                 215                 220
Leu Ser Ser Ala Met Trp Ala Lys Val Leu Thr Ser Phe Thr Asn Lys
225                 230                 235                 240
Glu Leu Gln Ala Tyr Ala Lys Ala Gly Ala Val Ala Glu Glu Val Leu
                245                 250                 255
Ala Ala Ile Arg Thr Val Ile Ala Phe Gly Gly Gln Lys Lys Glu Leu
            260                 265                 270
Glu Arg Tyr Asn Lys Asn Leu Glu Glu Ala Lys Arg Val Gly Ile Lys
    275                 280                 285
Lys Ala Ile Thr Ala Asn Ile Ser Ile Gly Ile Ala Tyr Leu Leu Val
    290                 295                 300
Tyr Ala Ser Tyr Ala Leu Ala Phe Trp Tyr Gly Thr Ser Leu Val Leu
305                 310                 315                 320
Ser Asn Glu Tyr Ser Ile Gly Gln Val Leu Thr Val Phe Phe Ser Ile
                325                 330                 335
Leu Leu Gly Thr Phe Ser Ile Gly His Leu Ala Pro Asn Ile Glu Ala
            340                 345                 350
Phe Ala Asn Ala Arg Gly Ala Ala Tyr Glu Ile Phe Lys Ile Ile Asp
    355                 360                 365
Asn Glu Pro Ser Ile Asp Ser Phe Ser Thr Lys Gly His Lys Pro Asp
370                 375                 380
Ser Ile Met Gly Asn Leu Glu Phe Lys Asn Val Tyr Phe Asn Tyr Pro
385                 390                 395                 400
Ser Arg Ser Glu Val Lys Ile Leu Lys Gly Leu Asn Leu Lys Val Lys
                405                 410                 415
Ser Gly Gln Thr Val Ala Leu Val Gly Asn Ser Gly Cys Gly Lys Ser
            420                 425                 430
Thr Thr Val Gln Leu Leu Gln Arg Leu Tyr Asp Pro Ile Glu Gly Glu
    435                 440                 445
Val Ser Ile Asp Gly Gln Asp Ile Arg Thr Ile Asn Val Arg Tyr Leu
    450                 455                 460
Arg Glu Ile Ile Gly Val Val Ser Gln Glu Pro Val Leu Phe Ala Thr
465                 470                 475                 480
Thr Ile Ala Glu Asn Ile Arg Tyr Gly Arg Glu Asn Val Thr Met Asp
                485                 490                 495
Glu Ile Glu Lys Ala Val Lys Glu Ala Asn Ala Tyr Asp Phe Ile Met
            500                 505                 510
Lys Leu Pro His Lys Phe Asn Thr Leu Val Gly Glu Arg Gly Ala Gln
    515                 520                 525
```

-continued

Leu Ser Gly Gly Gln Lys Gln Arg Ile Ala Ile Ala Arg Ala Leu Val
    530                 535                 540

Arg Asn Pro Lys Ile Leu Leu Asp Glu Ala Thr Ser Ala Leu Asp
545                 550                 555                 560

Thr Glu Ser Glu Ala Val Val Gln Ala Ala Leu Asp Lys Ala Arg Glu
                565                 570                 575

Gly Arg Thr Thr Ile Val Ile Ala His Arg Leu Ser Thr Val Arg Asn
                    580                 585                 590

Ala Asp Val Ile Ala Gly Phe Asp Gly Gly Val Ile Val Glu Gln Gly
                595                 600                 605

Asn His Glu Glu Leu Met Lys Glu Lys Gly Ile Tyr Phe Lys Leu Val
        610                 615                 620

Met Thr Gln Thr Arg Gly Asn Glu Ile Glu Pro Gly Asn Asn Ala Tyr
625                 630                 635                 640

Glu Ser Gln Ser Asp Thr Gly Ala Ser Glu Leu Thr Ser Glu Lys Ser
                    645                 650                 655

Lys Ser Pro Leu Ile Arg Arg Ser Ile Arg Arg Ser Ile His Arg Arg
                660                 665                 670

Gln Asp Gln Glu Arg Arg Leu Ser Ser Lys Glu Asp Val Asp Glu Asp
        675                 680                 685

Val Pro Met Val Ser Phe Trp Gln Ile Leu Lys Leu Asn Ile Ser Glu
        690                 695                 700

Trp Pro Tyr Leu Val Val Gly Val Leu Cys Ala Val Ile Asn Gly Cys
705                 710                 715                 720

Ile Gln Pro Val Phe Ala Ile Val Phe Ser Lys Ile Val Gly Val Phe
                    725                 730                 735

Ser Arg Asp Asp Asp His Glu Thr Lys Gln Arg Asn Cys Asn Leu Phe
                740                 745                 750

Ser Leu Leu Phe Leu Val Met Gly Met Ile Ser Phe Val Thr Tyr Phe
        755                 760                 765

Phe Gln Gly Phe Thr Phe Gly Lys Ala Gly Glu Ile Leu Thr Lys Arg
        770                 775                 780

Leu Arg Tyr Met Val Phe Lys Ser Met Leu Arg Gln Asp Ile Ser Trp
785                 790                 795                 800

Phe Asp Asp His Lys Asn Thr Thr Gly Ser Leu Thr Thr Arg Leu Ala
                    805                 810                 815

Ser Asp Ala Ser Asn Val Lys Gly Ala Met Gly Ser Arg Leu Ala Val
                820                 825                 830

Val Thr Gln Asn Val Ala Asn Leu Gly Thr Gly Ile Ile Leu Ser Leu
        835                 840                 845

Val Tyr Gly Trp Gln Leu Thr Leu Leu Val Val Ile Ile Pro Leu
        850                 855                 860

Ile Val Leu Gly Gly Ile Ile Glu Met Lys Leu Leu Ser Gly Gln Ala
865                 870                 875                 880

Leu Lys Asp Lys Lys Glu Leu Glu Ile Ser Gly Lys Ile Ala Thr Glu
                    885                 890                 895

Ala Ile Glu Asn Phe Arg Thr Val Val Ser Leu Thr Arg Glu Gln Lys
                900                 905                 910

Phe Glu Thr Met Tyr Ala Gln Ser Leu Gln Ile Pro Tyr Arg Asn Ala
        915                 920                 925

Leu Lys Lys Ala His Val Phe Gly Ile Thr Phe Ala Phe Thr Gln Ala
        930                 935                 940

```
Met Ile Tyr Phe Ser Tyr Ala Ala Cys Phe Arg Phe Gly Ala Tyr Leu
945                 950                 955                 960

Val Ala Arg Glu Leu Met Thr Phe Glu Asn Val Met Leu Val Phe Ser
                965                 970                 975

Ala Val Val Phe Gly Ala Met Ala Ala Gly Asn Thr Ser Ser Phe Ala
                980                 985                 990

Pro Asp Tyr Ala Lys Ala Lys Val Ser Ala Ser His Ile Ile Arg Ile
            995                 1000                1005

Ile Glu Lys Ile Pro Glu Ile Asp Ser Tyr Ser Thr Glu Gly Leu Lys
        1010                1015                1020

Pro Asn Trp Leu Glu Gly Asn Val Lys Phe Asn Gly Val Met Phe Asn
025                 1030                1035                1040

Tyr Pro Thr Arg Pro Asn Ile Pro Val Leu Gln Gly Leu Ser Phe Glu
                1045                1050                1055

Val Lys Lys Gly Gln Thr Leu Arg Leu Val Gly Ser Ser Gly Cys Gly
                1060                1065                1070

Lys Ser Thr Val Val Gln Leu Leu Glu Arg Phe Tyr Asn Pro Met Ala
            1075                1080                1085

Gly Thr Val Phe Leu Asp Gly Lys Glu Ile Lys Gln Leu Asn Val Gln
    1090                1095                1100

Trp Leu Arg Ala His Leu Gly Ile Val Ser Gln Glu Pro Ile Leu Phe
105                 1110                1115                1120

Asp Cys Ser Ile Thr Glu Asn Ile Ala Tyr Gly Asp Asn Ser Arg Val
                1125                1130                1135

Val Ser His Glu Glu Ile Val Arg Ala Ala Arg Glu Ala Asn Ile His
            1140                1145                1150

Gln Phe Ile Asp Ser Leu Pro Glu Lys Tyr Asn Thr Arg Val Gly Asp
        1155                1160                1165

Lys Gly Thr Gln Leu Ser Gly Gly Gln Lys Gln Arg Ile Ala Ile Ala
        1170                1175                1180

Arg Ala Leu Val Arg Gln Pro His Ile Leu Leu Leu Asp Glu Ala Thr
185                 1190                1195                1200

Ser Ala Leu Asp Thr Glu Ser Glu Lys Val Val Gln Glu Ala Leu Asp
                1205                1210                1215

Lys Ala Arg Glu Gly Arg Thr Cys Ile Val Ile Ala His Arg Leu Ser
            1220                1225                1230

Thr Ile Gln Asn Ala Asp Leu Ile Val Val Ile Gln Asn Gly Gln Val
        1235                1240                1245

Lys Glu His Gly Thr His Gln Gln Leu Leu Ala Gln Lys Gly Ile Tyr
    1250                1255                1260

Phe Ser Met Val Gln Ala Gly Ala Lys Arg Ser
265                 1270                1275
```